(12) United States Patent
Takeuchi et al.

(10) Patent No.: US 6,184,365 B1
(45) Date of Patent: Feb. 6, 2001

(54) ANTHRACYCLINE DERIVATIVES HAVING 4-AMINO-2,4,6-TRIDEOXY-2 FLUORO-α-L-TALOPYRANOSYL GROUP

(75) Inventors: Tomio Takeuchi; Sumio Umezawa, both of Tokyo; Tsutomu Tsuchiya; Yasushi Takagi, both of Yokohama, all of (JP)

(73) Assignee: Zaidan Hojin Biseibutsu Kagaku Kenkyu Kai, Tokyo (JP)

( * ) Notice: Under 35 U.S.C. 154(b), the term of this patent shall be extended for 0 days.

(21) Appl. No.: 08/991,436

(22) Filed: Dec. 16, 1997

(30) Foreign Application Priority Data

Feb. 16, 1996 (JP) .................................................. 8-335913

(51) Int. Cl.⁷ .................................. C07H 1/00; C07H 5/00

(52) U.S. Cl. ........................ 536/17.2; 536/6.4; 536/18.5; 536/18.7; 536/122

(58) Field of Search ..................... 536/6.4, 1.11, 536/17.2, 18.7, 18.5, 122; 514/34

(56) References Cited

U.S. PATENT DOCUMENTS

| | | | |
|---|---|---|---|
| 4,427,664 | * | 1/1984 | Hondon et al. ................ 514/34 |
| 4,987,126 | * | 1/1991 | Bargiotti et al. .............. 514/34 |
| 5,719,130 | * | 2/1998 | Takeuchi et al. ............. 514/34 |

FOREIGN PATENT DOCUMENTS

WO97/00880   9/1997   (WO) .

OTHER PUBLICATIONS

Chemical Abstracts, Columbus, Ohio, vol. 126, No. 13, Mar. 25, 1997, Abstract No. 171841z.
Patent Abstracts of Japan, JP 06 256377 A (*Microbial. Chem. Res. Found*), Sept. 13, 1994.

\* cited by examiner

*Primary Examiner*—Elli Peselev
(74) *Attorney, Agent, or Firm*—Larson & Taylor

(57) ABSTRACT

7-O-(4-Amino-2,4,6-trideoxy-2-fluoro-α-L-talopyranosyl)-daunomycinone or -adriamycinone is now synthesized as a novel daunomycinone or adriamycinone derivative having the general formula (I)

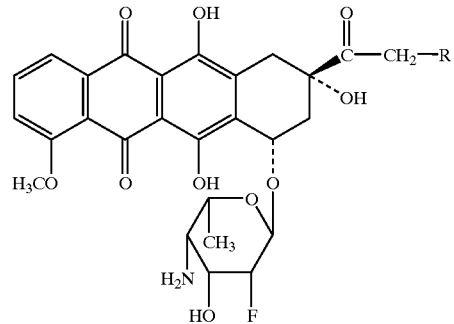

wherein R is a hydrogen atom or hydroxyl group. These novel compounds according to this invention exhibit excellent antitumor activities and have a high solubility in water, and hence they are useful as an antitumor agent.

3 Claims, No Drawings

ANTHRACYCLINE DERIVATIVES HAVING 4-AMINO-2,4,6-TRIDEOXY-2 FLUORO-α-L-TALOPYRANOSYL GROUP

FIELD OF THE INVENTION

This invention relates to novel and water-soluble anthracycline derivatives which exhibit an excellent anticancer or antitumor activity at a low dosage thereof and which have 4-amino-2,4,6-trideoxy-2-fluoro-α-L-talopyranosyl group as the sugar moiety. This invention also relates to processes for the preparation of said novel anthracycline derivatives and further to a pharmaceutical composition comprising the same as an active ingredient. More particularly, this invention relates to 7-O-(4-amino-2,4,6-trideoxy-2-fluoro-α-L-talopyranosyl)daunomycinone and 7-O-(4-amino-2,4,6-trideoxy-2-fluoro-α-L-talopyranosyl)-adriamycinone or their acid addition salts as the novel and water-soluble anthracycline derivatives having an anticancer or antitumor activity and a low toxicity. This invention also relates to a pharmaceutical composition containing the novel anthracycline derivative or an acid addition salt thereof. Further, this invention relates to processes for the preparation of these novel anthracycline derivatives. Yet further, this invention relates to a novel compound useful as an intermediate for the synthesis of these novel anthracycline derivatives.

BACKGROUND OF THE INVENTION

As antibiotics of the anthracycline type are known daunomycin which is also named daunorubicin in the specification of U.S. Pat. No. 3,616,242, as well as adriamycin which is also named doxorubicin in the specification of U.S. Pat. No. 3,590,028. These compounds have broad anticancer spectra against experimental tumors and have widely been utilized for clinical purposes as a chemotherapeutic anticancer agent.

While, daunomycin and adriamycin can exhibit a somewhat strong anticancer or antitumor activity against various kinds of cancers or tumors, but are not necessarily satisfactory as the anticancer agent or antitumor agent. That is, daunomycin and adriamycin have been utilized widely as a chemotherapeutic anticancer agent for clinical treatment of cancer-bearing patients, but they are also known to bring about serious side-effects such as leukocytopenia, alopecia, myocardiopathy and others, in many instances.

Therefore, it has hitherto been attempted to produce newly a variety of novel daunomycin-related compounds with the intention of providing such novel daunomycin-related compounds which would have a much enhanced anticancer or antitumor activity but with exhibiting a low toxicity. As some outcome of the attempts hitherto made, there have been proposed several compounds, for example, those known as aclacinomycins A and B; 4'-O-tetrahydropyranyl-adriamycin; N-monobenzyl- or N-dibenzyl-adriamycin.

Besides, U.S. Pat. No. 4,427,664 specification discloses 7-O-(3,4-di-O-acetyl-2,6-dideoxy-2-iodo-α-L-mannohexopyranosyl)daunomycinone and 7-O-(3,4-di-O-acetyl-2,6-dideoxy-2-iodo-α-L-talo-hexopyranosyl) daunomycinone.

We, the present inventors, proceeded with our investigations in an attempt to provide novel derivatives of daunomycin and adriamycin which will exhibit a higher anticancer or antitumor activity than those of daunomycin or adriamycin but with a low toxicity. As a part of our investigations, we have already synthesized some derivatives of daunomycin and adriamycin in which the sugar moiety of daunomycin and adriamycin has been chemically modified. For example, the present inventors already reported 4'-O-tetrahydropyranyl-daunomycin or -adriamycin as well as 3'-deamino-3'-morpholino-daunomycin or -adriamycin.

Further, the present inventors succeeded in synthesizing such anthracycline derivatives having antitumor activities which are represented by the following general formula (A)

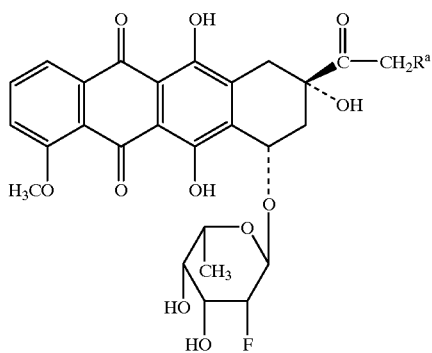

(A)

wherein $R^a$ stands for a hydrogen atom or a hydroxyl group, that is, 7-O-(2,6-dideoxy-2-fluoro-α-L-talopyranosyl)-daunomycinone and 7-O-(2,6-dideoxy-2-fluoro-α-L-talopyranosyl)-adriamycinone, which possess an anticancer or antitumor activity (see Japanese Patent Publication "Kokoku" Hei 6-31298 and European Patent No. 0230013).

The present inventors also succeeded in synthesizing such anthracycline derivatives having antitumor activities which are represented by the following general formula (B)

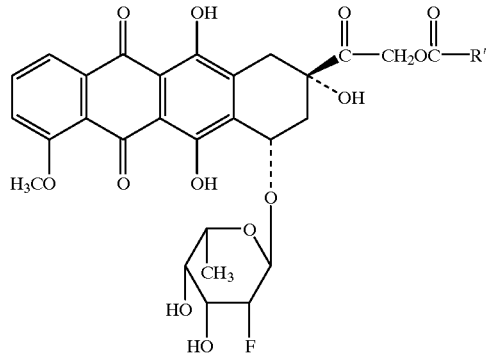

(B)

wherein R' stands for a group —$(CH_2)_m$—H where m is an integer of 1~6,or R' stands for a group —$(CH_2)_n$—COOH where n is an integer of 1~10 (see Japanese Patent Publication "Kokoku" Hei 7-42304 and European Patent No. 0275431).

The present inventors further succeeded in synthesizing such anthracycline derivatives having antitumor activities which are represented by the following general formula (C)

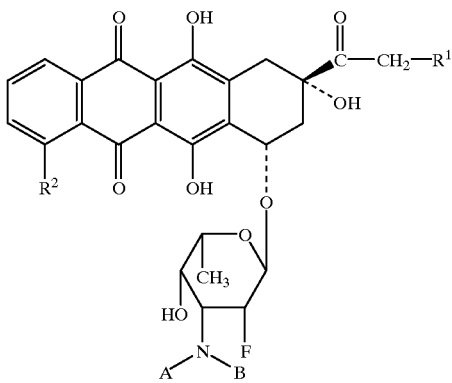

(C)

wherein $R^1$ is a hydrogen atom or a hydroxyl group, $R^2$ is a methoxy group or a hydrogen atom, and A and B each stand for a hydrogen atom or A and B as taken together form a chain of formula —$CH_2$—$CH_2$—O—$CH_2$—$CH_2$— (see Japanese Patent Application First Publication "Kokai" Sho-64-203397). As examples of the anthracycline derivatives of the general formula (C), there may be mentioned 7-O-(3-amino-2,3,6-trideoxy-2-fluoro-α-L-talopyranosyl)daunomycinone; 7-O-(3-amino-2,3,6-trideoxy-2-fluoro-α-L-talopyranosyl)adriamycinone; 7-O-(2,3,6-trideoxy-2-fluoro-3-morpholino-α-L-talopyranosyl)adriamycinone and others.

7-O-(2,6-Dideoxy-2-fluoro-α-L-talopyranosyl)adriamycinone, as one of the anthracycline derivatives of the general formula (A) given above, exhibits a remarkable antitumor activity, but is barely soluble in water, so that it had a difficulty in formulating into injection preparations. Then, the anthracycline derivatives of general formulae (B) and (C) above have been synthesized in an attempt to give such anthracycline derivatives which have an improved solubility in water. Amongst the derivatives of the general formula (C), 7-O-(3-amino-2,3,6-trideoxy-2-fluoro-α-L-talopyranosyl)adriamycinone is soluble in water, but the antitumor activity thereof has not been recognized to be remarkably higher than that of adriamycine, even though the former has the antitumor activity a little higher than that of the latter.

The present inventors further have continued our investigations in various ways with the intention of producing such novel anthracycline derivatives which can exhibit higher anticancer or antitumor activities than those of daunomycin, adriamycin and the antitumor anthracycline derivatives of the general formulae (A), (B) and (C) above, even at a low dosage, and which are of satisfactory solubility in water and of low toxicity.

The anticancer or antitumor activities of the anthracycline derivatives of the general formulae (A) and (B) above are, in fact, noticeably superior to those of daunomycin and adriamycin, but are not yet satisfactorily high enough. All of the anthracycline derivatives of the general formula (C) above are soluble in water, but most of those derivatives exhibit only an anticancer or antitumor activity substantially as high as or lower than that of adriamycin.

Therefore, there still exists a desire for providing such novel anthracycline derivatives which can exhibit higher anticancer or antitumor activities than those of the known anthracycline derivatives. Further, in general, it is always convenient for clinical applications to administer the anticancer or antitumor compounds in the form of injectable preparations. Thus, for the purpose of therapeutic treatments of a variety of cancers and tumors, a demand always exists in the art to provide and explore such novel anticancer or antitumor agents having a nature that they can exhibit a strong anticancer or antitumor activity but with low toxicity and also they are highly soluble in water.

In order to solve the problems above-mentioned, the present inventors have proceeded with our further investigations in an attempt to synthesize novel anthracycline derivatives having a new fluorinated amino-sugar moiety. As a result of these further investigations, we have now succeeded in synthesizing 1-O-acetyl derivative of 4-amino-2,4,6-trideoxy-2-fluoro-α-L-mannopyranose and 4-amino-2,4,6-trideoxy-2-fluoro-α-L-mannopyranosyl bromide or their 3,4-di-O,N-protected derivatives as new compounds through a multi-step method with starting from methyl 4-O-benzyl-2,6-dideoxy-2-fluoro-α-L-talopyranoside which has been obtained in the synthesis of the anthracycline derivative of the general formula (A) shown hereinbefore (see the specification of Japanese patent application No. Hei-7-179621 filed Jun. 23, 1995 which is corresponding to PCT application No. PCT/JP96/01697 filed Jun. 19, 1996, now published under International publication No. WO 97/00880).

Then, by utilizing these 4-amino-2,4,6-trideoxy-2-fluoro-α-L-mannopyranose derivatives as synthesized for the first time and by taking such a method which comprises condensing the 4-amino-2,4,6-trideoxy-2-fluoro-α-L-mannopyranosyl group with the 7-hydroxyl group of daunomycinone or adriamycinone, we have earlier succeeded in synthesizing such novel daunomycinone derivative and adriamycinone derivative which are represented by the following general formula (D)

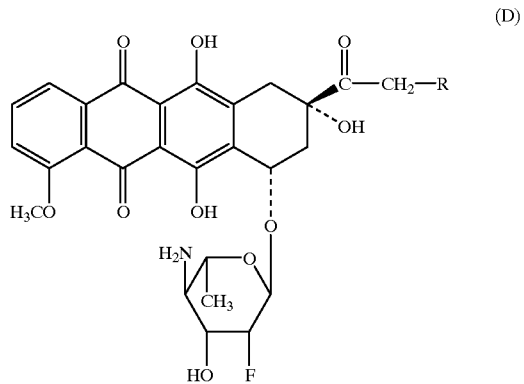

(D)

wherein R is a hydrogen atom or a hydroxyl group or an acid addition salt thereof, as such anthracycline derivatives which bear as the sugar moiety a 4-amino-2,4,6-trideoxy-2-fluoro-α-L-mannopyranosyl group where the amino group at the 4-position of this sugar moiety is of the equatorial direction. Furthermore, we have found that the novel anthracycline derivatives of the general formula (D) above are soluble in water, that they exhibit a high anticancer or antitumor activity even when they are administered to test animals at low dosages, and that development of acute toxicity does not take place in the test animals having received the administration of the anthracycline derivative of the formula (D) at the low dosages which can give high anticancer or antitumor effects in the test animals so treated (see the aforesaid Japanese patent application No. Hei-7-179621).

The daunomycinone or adriamycinone derivative of the general formula (D) contains the equatorically directed amino group at the 4-position of the sugar moiety thereof, and particular examples thereof include Compound (a) and Compound (b) of the following formulae (D-a) and (D-b), respectively.

(1) Compound (a): 7-O-(4-amino-2,4,6-trideoxy-2-fluoro-α-L-mannopyranosyl)daunomycinone of the following formula

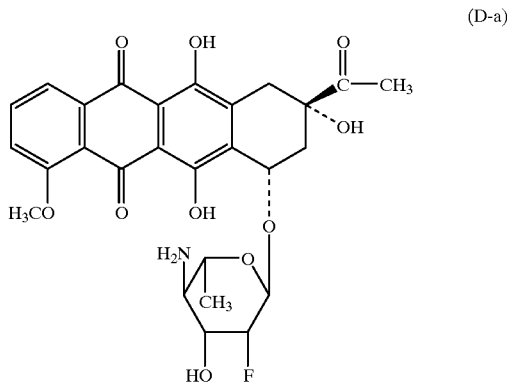

(D-a)

(2) Compound (b): 7-O-(4-amino-2,4,6-trideoxy-2-fluoro-α-L-mannopyranosyl)adriamycinone of the following formula

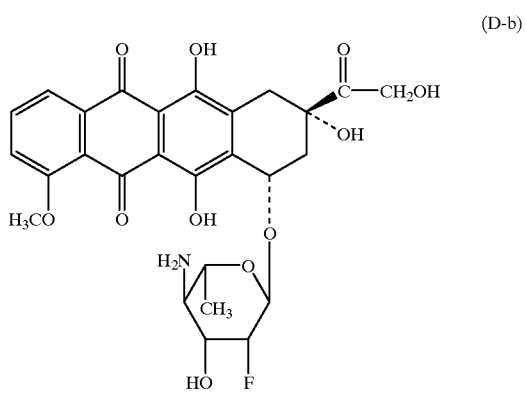

(D-b)

It has been confirmed through "in vivo" tests that, among the anthracycline derivatives of the general formula (D) above, 7-O-(4-amino-2,4,6-trideoxy-2-fluoro-α-L-mannopyranosyl)adriamycinone of the formula (D-b) exhibits a remarkably high antitumor activity against experimental tumors in animals and has a remarkably improved antitumor activity against mouse Leukemia L-1210 cell over adriamycin even when the compound of the formula (D-b) is administered at low dosages. While, it has also been found that althoguh the compound of the formula (D-b) is soluble in water and exhibits the above-mentioned excellent antitumor activity against mouse Leukemia L-1210 cell, this compound as tested in "in vitro" tests remains to exhibit against various human cancer cells such anticancer activities which are substantially as high as those of adriamycin.

Accordingly, one of the objects of this invention is to provide and explore new anticancer anthracycline derivatives having such properties that they can exhibit an excellent anticancer or antitumor activity and especially exhibit a stronger anticancer activity against various human cancer cells than adriamycin but they have a low toxicity and a high solubility in water.

DETAILED DESCRIPTION OF THE INVENTION

In order to achieve the above objects of this invention, the present inventors have continued further investigations in an attempt to synthesize and provide such novel anthracycline derivatives which are able to have the above-mentioned excellent properties and contains a fluorinated amino-sugar moiety.

As a result of our further investigations above, the present inventors have now succeeded in synthesizing as new compounds, protected derivatives of 4-amino-2,4,6-trideoxy-2-fluoro-L-talopyranose having the axially directed 4-amino group, as well as 3,4-di-O,N-protected derivatives of 4-amino-2,4,6-trideoxy-2-fluoro-α-L-talopyranocyl bromide through a multi-staged process with starting from 3,4-di-O-acetyl-2,6-dideoxy-2-fluoro-α-L-talopyranosyl bromide which is a known compound described in the "Carbohydrate Research" Vol. 169, pages 69–81 (1987).

The present inventors also have now succeeded in synthetizing as a novel anthracycline derivative 7-O-(4-amino-2,4,6-trideoxy-2-fluoro-α-L-talopyranosyl)daunomycinone having the axially directed amino group at the 4-position of the sugar moiety thereof, by means of a process which comprises utilizing the above-mentioned derivatives of 4-amino-2,4,6-tridoexy-2-fluoro-L-talopyranose synthetized now newly as above, and condensing a 4-amino-2,4, 6-trideoxy-2-fluoro-α-L-talopyranosyl group with the 7-hydroxyl group of daunomycinone. The present inventors have now succeeded also in synthetizing as a novel anthracycline derivative 7-O-(4-amino-2,4,6-trideoxy-2-fluoro-α-L-talopyranosyl)adriamycinone from the new daunomycinone derivative mentioned just above. Furthermore, the present inventors have now found that the two particular, novel anthracycline derivatives now synthetized and specified just above have a high solubility in water to such extent that these novel two anthracycline derivatives can dissolve in amounts of 10 mg and 15 mg, respectively, per 1 ml of water, that these novel two anthracycline derivatives may be formulated into an aqueous injection preparation, and that these novel two anthracycline derivatives as administered even at low dosages are not only able to exhibit an antitumor activity against mouse Leukemia L-1210 cell to a degree substantially equal to or higher than that of adriamycin but also are able to exhibit remarkably improved anticancer activities against various human cancer cells in "in vitro" tests, in comparison with adriamycin. On the basis of these findings obtained by the present inventors, this invention has now been accomplished.

In a first aspect of this invention, therefore, there is provided a daunomycinone or adriamycinone derivative represented by the following general formula

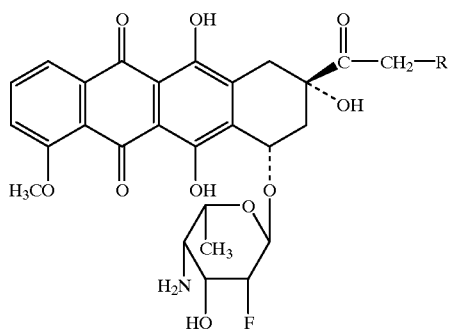

(I)

wherein R is a hydrogen atom or a hydroxyl group, or a pharmaceutically acceptable acid addition salt thereof.

As examples of the pharmaceutically acceptable acid addition salts of the daunomycinone or adriamycinone derivative of the general formula (I), there are mentioned such acid addition salts which may be formed by reacting the 4'-amino group of said derivative with a pharmaceutically acceptable inorganic acid such as hydrochloric acid, sulfuric acid and phosphoric acid, or a pharmaceutically acceptable organic acid such as acetic acid, propionic acid, citric acid, lactic acid, methanesulfonic acid in a usual manner.

Examples of the daunomycinone or adriamycinone derivatives of the general formula (I) include the undermentioned Compound (a) and Compound (b) of this invention:

(1) Compound (a): 7-O-(4-amino-2,4,6-trideoxy-2-fluoro-α-L-talopyranosyl)daunomycinone (see Example 1 hereinafter given) represented by the following formula

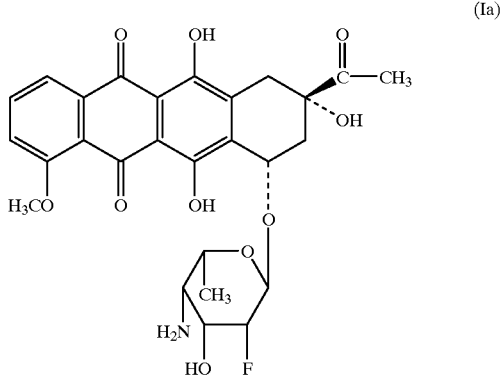

(Ia)

(2) Compound (b): 7-O-(4-amino-2,4,6-trideoxy-2-fluoro-α-L-talopyranosyl)adriamycinone (see Example 2 hereinafter given) represented by the following formula

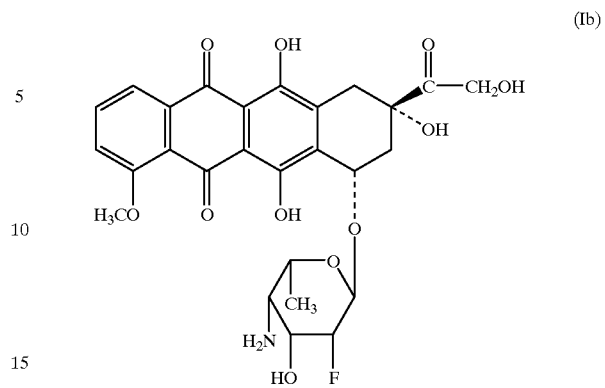

(Ib)

Now, some Test Examples are given to illustrate the antitumor activities of Compound (a) of formula (Ia) and Compound (b) of formula (Ib) shown above, which are embraced by the anthracycline derivatives of the general. formula (I) according to the first aspect of this invention.

TEST EXAMPLE 1

In this Example, some tests were made to demonstrate antitumor activities of the compounds of this invention shown against leukemia in $CDF_1$ mice as induced by a mouse leukemia, Leukemia L-1210 cells.

Thus, to evaluate the antitumor effects of the novel compounds of this invention against experimental tumors in animals, $CDF_1$ mice (four mice per group) were intraperitoneally inoculated with cells of Leukemia L-1210 at an amount of $1 \times 10^5$ cells/mouse. Since an elapse of 24 hours from the inoculation of the leukemia cells, a test compound of this invention was administered intraperitoneally to the mice under test once a day for consecutive 9 days, with the test compound being given as its hydrochloride in the form of a solution in a physiological saline. The mice so treated were observed for 60 days after the administration of the test compound. In the meanwhile, mice of the control group (the untreated group) were administered only with physiological saline after the inoculation of the L-1210 cells. During the observation period, the number of the surviving mice was counted for both the treated group and the control group, and the mean survival days of mice of both the treated group and the control group were calculated. Then, the percentages (%) of the increase in the life-span of the treated mice was estimated, as T/C (%), in terms of the mean survival day (C) of the untreated mice of the control group and the mean survival day (T) of the treated mice of the treated group. For comparison purposes, similar tests were effected using daunomycin (as hydrochloride) and adriamycin (as hydrochloride). The test results are shown in Table 1 below. The mean survival day of mice of the control group (the untreated group) was 8 to 9 days, and the mean survival day of mice of the comparative groups having received the administration of daunomycin or adriamycin usually varied dependently on the dosage of the compound tested.

In Table 1 below, the symbol ">" indicates that, among the four mice under test which were inoculated with the tumor cells and then administered with the compound under test, there existed at least one mouse which could be cured and survived for 60 days or longer by the administration of the test compound in spite of their received inoculation of tumor cell. Incidentally, in respect of the fractional numbers parenthesized below the numerical values of increase (%) in the life-span, the denominator of the fraction denotes the number of mice tested in one test group but the numerator of the fraction denotes the number of mice which survived for 60 days or longer.

TABLE 1

| | Increase (%) in life-span (T/C, %) Dosage (mg/kg/day) | | | | | |
|---|---|---|---|---|---|---|
| Compound tested | 5 | 2.5 | 1.25 | 0.6 | 0.3 | 0.15 |
| 7-O-(4-amino-2,4,6-trideoxy-2-fluoro-α-L-talopyranosyl)daunomycinone [Compound (a) of this invention] (as hydrochloride) | 175* | 235* | >463 (2/4) | 182 | 152 | 127 |
| 7-O-(4-amino-2,4,6-trideoxy-2-fluoro-α-L-talopyranosyl)adriamycinone [Compound (b) of this invention] (as hydrochloride) | 92* | 139* | >330* (1/4) | >403 (1/4) | >400 (1/4) | 155 |
| Daunomycinone (as hydrochloride) (Comparative) | 138* | 171* | 158 | 145 | 112 | 132 |
| Adriamycin (as hydrochloride) (Comparative) | 177* | 273* | 330 | 208 | 132 | 140 |

Notes:
Asterisks (*) indicate that development of toxicity such as toxicity-related death or a body weight loss was observed on the corresponding mice tested.

In the "in vivo" tests as described above, the daunomycinone derivative of general formula (I) according to the first aspect of this invention, namely Compound (a) of this invention as given at a dosage in a range of 0.6~1.25 mg/kg was able to exhibit antitumor activities higher than those of daunomycin. On the other hand, it is found that Compound (b) of this invention, namely the adriamycin derivative as given at a low dosage in a range of 0.3 mg/kg~0.6 mg/kg was able to exhibit such remarkably high antitumor activities that the percentage of the increase in the life-span (T/C, %) was as high as a value of greater than 400% to a value of greater than 403% and that the number of the mice surviving for 60 days (the mice as fully cured from the leukemia) amounted to two in eight. This indicates that Compound (b) given at a dosage of 0.3~0.6 mg/kg was able to exhibit markedly enhanced anticancer or antitumor activities, as compared with those of adriamycin as given at a dosage of 0.3 mg/kg~0.6 mg/kg. It is also found that Compound (b) of this invention as given at the low dosage of 0.3 mg/kg to 0.6 mg/kg did not involve the development of toxicity. Furthermore, it is found that Compound (b) of this invention as given at a low dosage of 0.15 mg/kg to 0.6 mg/kg was able to exhibit remarkably enhanced anticancer or antitumor activities in terms of percentages of the increase in the life-span of the treated mice (T/C, %), in comparison with daunomycin.

Daunomycin or adriamycin used as the comparative drug in the above Test Example 1 is an anticancer agent which has been used clinically and practically administered to human beings at a dosage in the range of 0.4 mg/kg~2 mg/kg in dependent upon the nature of cancers to be treated. When daunomycin or adriamycin is administered at a dosage ranging from 2.5 mg/kg/day to 5 mg/kg/day to such mice as inoculated with the L-1210 cancer cells, daunomycin or adriamycin exhibits an anticancer or antitumor activities which amount to percentages of increase in the life-span (T/C, %) of 138%~273% or of about 330% at maximum, respectively, with being accompanied by the development of toxicity.

It is to be noticed that, in contrast to daunomycin or adriamycin, the adriamycinone derivative of the formula (Ib), namely Compound (b) of this invention, when administered at a proper low dosage in the range of 0.3~0.6 mg/kg/day to the mice as inoculated with the L-1210 cancer cells, is able to exhibit such extremely excellent antitumor effects that the development of toxicities is not involved, while the attainable values of percentages of increase in the life-span (T/C, %) are markedly higher than those attainable by daunomycin or adriamycin, and that particularly, the percentages of increase in the life-span can amount to about 400% or higher with involving a complete cure. Accordingly, Compounds (a) and (b) of this invention, particularly Compound (b), have such advantage that significant antitumor effects can be expected to be attained by them even when they are administered at a not too high dosage to the cancer-bearing patients for clinical treatments.

TEST EXAMPLE 2

Compound (a) of this invention or Compound (b) of this invention was added as the test compound at varying concentrations to different kinds of human cancer cells, mouse leukemia P388 cells or adriamycin-resistant P388 cells (P388/ADR) which had been incubated in test tubes containing an appropriate culture medium. The incubation of these cells was then continued for 72 hours from the addition of the test compound, and determination was made to evaluate such concentrations of the test compound which could inhibit the growth of the human cancer cells or mouse leukemia cells by 50% (namely, 50% inhibiting concentration; $IC_{50}$, µg/ml). Adriamycin was used as a comparative compound and was tested in the same manner as above.

The different kinds of human cancer cells tested were six kinds indicated below, including human chronic myelogenous leukemia (K562), human vaginal melanoma (HMV-1), human nasopharyngeal carcinoma (KB), human gastric adenocarcinoma (MKN-1), human lung non-small cell carcinoma (PC-14) and human bladder carcinoma (T24). The test results obtained are summarized in Table 2 below.

TABLE 2

| Test Compound | IC$_{50}$ (µg/ml) | | | | | | | |
|---|---|---|---|---|---|---|---|---|
| | K562 | HMV-1 | KB | MKN-1 | PC-14 | T24 | P388 | P388/ADR |
| 7-O-(4-Amino-2,4,6-trideoxy-2-fluoro-α-L-talopyranosyl)-daunomycinone [Compound (a) of this invention] (as hydrochloride) | 0.087 | 0.071 | 0.028 | 0.12 | 0.17 | 0.047 | <0.0098 | 0.086 |
| 7-O-(4-Amino-2,4,6-trideoxy-2-fluoro-α-L-talopyranosyl)-adriamycinone [Compound (b) of this invention] (as hydrochloride) | 0.063 | 0.056 | 0.023 | 0.062 | 0.12 | 0.026 | <0.0098 | 0.18 |
| Adriamycin (comparative) | 0.39 | 0.14 | 0.050 | 0.25 | 0.62 | 0.16 | 0.032 | 2.5 |

As will be clear from the test results of Table 2 above, it is evident that Compound (a) of this invention and Compound (b) of this invention can inhibit the growth of the different kinds of human cancer cells as well as mouse leukemia cancer P388 cells and P388/ADR cells and hence exhibit higher antitumor or anticancer activities than those of adriamycin. In particular, it should be worthy to note that Compound (b) of this invention exhibited against the human cancer cell MKN-1 an anticaner activity of 4-folds higher than that of adriamycin, against the human cancer cell PC-14 an anticancer activity of 5.2-folds higher than that of adriamycin, and against the human cancer cells K562 and T24 an anticancer activity of 6.2-folds higher than that of adriamycin. Further, it is seen that Compound (a) of this invention and Compound (b) of this invention exhibit against mouse leukemia P388/ADR cell anticancer activities of 29.1-folds and 13.9-folds higher than those of adriamycin, respectively.

As be clear from the foregoing, the novel anthracycline derivatives of the general formula (I) according to the first aspect of this invention exhibit the excellent antitumor activities and anticancer activities but are of low toxicity and are highly soluble in water.

Judging from the foregoing, it is expected that the novel anthracycline derivatives of the general formula (I) according to the first aspect of this invention, owing to their excellent antitumor activities and their high water-solubility, are very much useful as the antitumor agents to be used for clinical treatments, and that they are utilizable for therapeutic treatments of a variety of tumors, similarly to daunomycin or adriamycin. Accordingly, the compounds of the general formula (I) according to this invention can be used usefully as a therapeutic agent for tumors or cancers in the therapeutic treatments of solid cancers, ascitic cancers and the like.

According to a second aspect of this invention, therefore, there is provided a pharmaceutical composition, particularly an antitumor composition, characterized in that it comprises as an active ingredient a daunomycinone or adriamycinone derivative of the general formula (I) defined hereinbefore or a pharmaceutically acceptable acid addition salt thereof, in combination with a pharmaceutically acceptable carrier.

When the compound of the general formula (I) according to this invention is administered in practice, it may usually be administered orally or parenterally. It is thus feasible to administer the compound of this invention orally or parenterally after the compound is mixed with a pharmaceutically acceptable solid or liquid carrier which is used conventionally in the pharmaceutic field, followed by formulating the resulting mixture into various preparation forms such as powder, granules, tablets or syrups, or injections.

As a general method for the administration, the compound of this invention may be administered to animals in the form of an injectable preparation by intraperitoneal injection, subcutaneous injection, intravascular injection, either intravenous or intra-arterial, or local injection, and the like. For the administration to human beings, the compound of this invention may be administered in the form of an injectable preparation by intravascular injection, either intravenous or intra-arterial, or local injection, and the like. The compound of this invention may be administered consecutively or intermittently at such dosage and to such extent that the total dosage of the compound given would not exceed a certain level as determined in view of results of preliminary animal tests and various circumstances.

Of course, the administration of the compound of this invention should be carried out with changing the dosage of the compound appropriately in accordance with the way of administration and the conditions of the patients or animals to be treated, for example, age, body weight, sex, sensitivity, foods, administration time, administration route, drug(s) to be concurrently administered, and the seriousness of patients or their disease and others. The compound of this invention may be administered at a substantially same dose as or at a lower dose than that of daunomycin or adriamycin when the compound is given as an antitumor or anticancer agent. Optimum dosage and frequency of administration of the compound of this invention under certain specific conditions must be determined by medical experts through preliminary tests in view of the above-mentioned guidelines. These requirements for administration are similarly applied to the oral administration of the compound of this invention.

Now, processes for the preparation of the daunomycinone derivative or adriamycinone derivative of the general formula (I) according to the first aspect of this invention will be described below.

For the preparation of 7-O-(4-amino-2,4,6-trideoxy-2-fluoro-α-L-talopyranosyl)-daunomycinone or -adriamycinone represented by the general formula (I), it is necessary to use 1-O-acetyl derivative of a 3-O-protected-4-N-protected-4-amino-2,4,6-trideoxy-2-fluoro-α-L-talopyranose or a 3-O-protected-4-N-protected-4-amino-2,4,6-trideoxy-2-fluoro-α-L-talopyranosyl bromide or iodide which are each a new sugar compound. The respective steps (1)~(10) which are effected in the synthesis of these new sugar compounds are firstly explained below in brief. Referential Example 1 given hereinafter will describe in details the reactions which are involved in these respective steps of said synthetic process.

In the following descriptions, abbreviation Bn means benzyl group, and abbreviation Ac means acetyl group.

Step (1): A known compound, 3,4-di-O-acetyl-2,6-dideoxy-2-fluoro-α-L-talopyranosyl bromide [Compound (1)] having the following formula

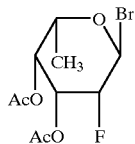

is reacted with benzyl alcohol in anhydrous benzene by König-Knorr synthesis method in the presence of silver carbonate, iodine and a powdery Molecular Sieves to benzyloxylate the 1-bromo group of Compound (1). Thereby, there is afforded as a main product benzyl 3,4-di-O-acetyl-2,6-dideoxy-2-fluoro-β-L-talopyranoside [Compound (2)] having the formula

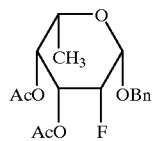

and there is also obtained as a subsidiary product benzyl 3,4-di-O-acetyl-2,6-dideoxy-2-fluoro-α-L-talopyranoside [Compound (3)] having the formula.

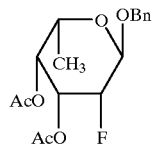

Step (2): Compound (2) is then treated with sodium methoxide in methanol for its deacetylation to yield benzyl 2,6-dideoxy-2-fluoro-β-L-talopyranoside [Compound (4)] having the formula

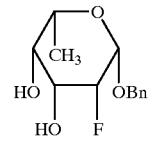

as the deacetylation product.

Step (3): Two hydroxyl groups of Compound (4) are reacted with dibutyltin oxide, followed by reaction with benzyl bromide. Thereby, benzyl 3-O-benzyl-2,6-dideoxy-2-fluoro-β-L-talopyranoside [Compound (5)] of the formula

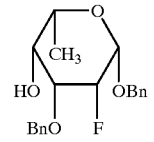

is obtained as a product of preferential benzylation of the 3-hydroxyl group of Compound (4).

Step (4): Compound (5) is oxidized with pyridinium chloro-chromate to produce benzyl 3-O-benzyl-2,6-dideoxy-2-fluoro-β-L-lyxo-hexopyranose-4-uloside [Compound(6)] of the formula

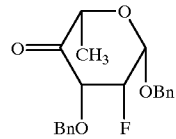

Step (5): Compound (6) is reacted with O-methylhydroxy-ammonium chloride in anhydrous dichloromethane to produce benzyl 3-O-benzyl-2,4,6-trideoxy-2-fluoro-4-(methoxyimino)-β-L-lyxo-hexopyranoside [Compound(7)] of the formula

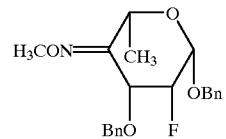

as the 4-methoxyiminoated product.

Step (6): Compound (7) is reduced with lithium borohydride in the presence of chlorotrimethylsilane to bring about the reduction with a steric selectivity and thus produce benzyl 4-amino-3-O-benzyl-2,4,6-trideoxy-2-fluoro-β-L-talo-pyranoside [Compound(8)] of the formula

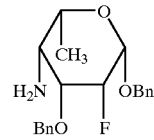

as a 4-amino-sugar having the L-talo configuration.

Step (7): Compound (8), without being purified, is reacted with trifluoroacetic anhydride to protect the amino group of Compound (8) with trifluoroacetyl group and thus produce benzyl 3-O-benzyl-2,4,6-trideoxy-2-fluoro-4-(trifluoroacetamido)-β-L-talopyranoside [Compound(9)] of the foumula

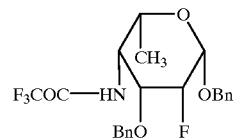

Step (8): Compound (9) is subjected to hydrogenolysis in the presence of a palladium catalyst to remove the two benzyl groups from Compound (9). Thereby, there is produced 2,4,6-trideoxy-2-fluoro-4-(trifluoroacetamido)-L-talopryranose [Compound(10)] having the formula

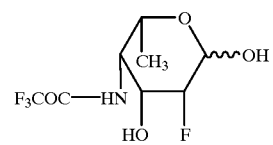

This Compound (10) is a mixture of the α-anomer [Compound (10-a)] and β-anomer [Compound(10-b)]. By subjecting Compound (10) to a silica gel column chromatography as developed with dichloromethane, the α-anomer [Compound (10-a)] can be isolated from the β-anomer [Compound(10-b)].

Step (9): Compound (10) (namely, the mixture of the α-anomer and β-anomer) is acetylated with acetic anhydride in anhydrous pyridine to produce an anomer mixture of 1,3-di-O-acetyl-2,4,6-trideoxy-2-fluoro-4-(trifluoroacetamido)-α-L-talopyranose [Compound(11)] having the formula

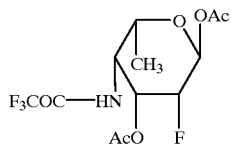

and 1,3-di-O-acetyl-2,4,6-trideoxy-2-fluoro-4-(trifluoroacetamido)-β-L-talopyranose [Compound(12)] having the formula

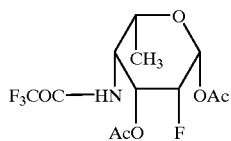

When this anomer mixture is subjected to a silica gel column chromatography as developed with chloroform-acetone (30:1) as the development solvent, Compound (11) and Compound (12) can be separated from each other as syrupy substances.

Step (10): The mixture of Compound (11) and Compound (12) (namely, said mixture of the α-anomer and β-anomer) is brominated with a solution of hydrogen bromide in acetic acid in a usual manner to afford 3-O-acetyl-2,4,6-trideoxy-2-fluoro-4-(trifluoroacetamido)-α-L-talopyranosyl bromide [Compound(13)] having the formula

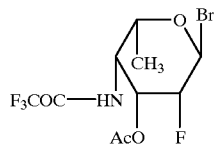

as a 1-bromo-sugar. Incidentally, when the anomer mixture of Compounds (11) and (12) is reacted with iodotrimethylsilane in anhydrous toluene, there may be obtained a corresponding 1-iodo-sugar.

The above-mentioned Compound (10), Compound (11), Compound (12) and Compound (13) are new compounds.

Similarly to that Compound (13) can be produced from Compounds (11), (12) by bromination of the latter, iodination of Compounds (11), (12) by an appropriate iodinating agent can produce the corresponding 1-iodo-sugar. Besides, in place of the acetyl group which has protected the 3-hydroxyl group in Compound (13), it is possible to introduce into said 3-hydroxyl group a benzoyl group as another proper hydroxyl-protecting group.

That is to say, when the aforesaid Compound (10) is treated with benzoyl chloride in pyridine, it is feasible to obtain 1,3-di-O-benzoyl-2,4,6-trideoxy-2-fluoro-4-(trifluoroacetamido)-L-talopyranose. The latter compound may be brominated by treatment with a solution of hydrogen bromide in acetic acid in a similar way to the aforesaid step (10) to give 3-O-benzoyl-2,4,6-trideoxy-2-fluoro-4-(trifluoroacetamido)-α-L-talopyranosyl bromide.

For the preparation of 7-O-(4-amino-2,4,6-trideoxy-2-fluoro-α-L-talopyranosyl)daunomycinone of formula (Ia) according to the first aspect of this invention, i.e. Compound (a) of this invention, there may be conducted such a process which comprises reacting the 7-hydroxyl group of daunomycinone with the aforesaid bromide compound (13), or generally with a 3,4-di-O,N-protected-4-amino-2,4,6-trideoxy-2-fluoro-α-L-talopyranosyl halide, for the condensation reaction, followed by removing the hydroxyl-protecting group and/or the amino-protecting group, where remaining, from the resulting condensation product by a conventional method. In this process, it is convenient to adopt such a procedure wherein compound (13) and daunomycinone are dissolved in anhydrous dichloroethane, the resultant solution is then subjected to the condensation reaction in the presence of mercuric bromide or iodide, yellow mercuric oxide and Molecular Sieves 3A, followed by recovering the resulting α-L-condensation product from the reaction solution and then removing the remaining acetyl and trifluoroacetyl groups as the protecting groups by alkaline hydrolysis, thereby to produce Compound (a) of this invention (see Example 2 given hereinafter).

According to a third aspect of this invention, more generally, there is provided a process for the preparation of 7-O-(4-amino-2,4,6-trideoxy-2-fluoro-α-L-talopyranosyl)-daunomycinone represented by the following formula

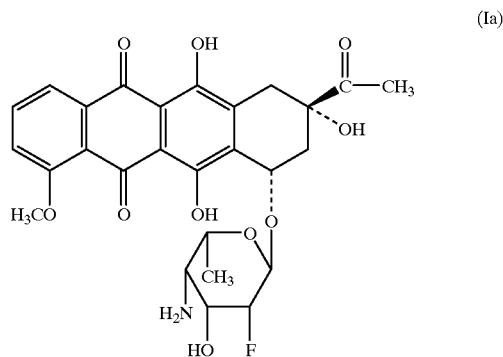

which comprises condensing daunomycinone represented by the following formula

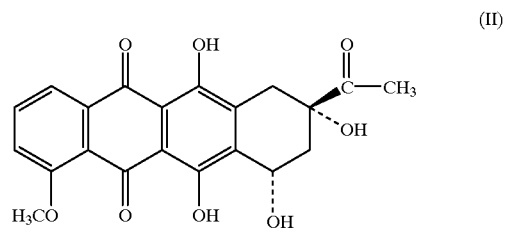

with a 3,4-di-O,N-protected-4-amino-2,4,6-trideoxy-2-fluoro-L-talopyranosyl halide represented by the following formula

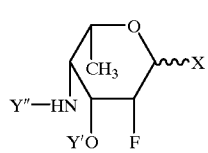

(III)

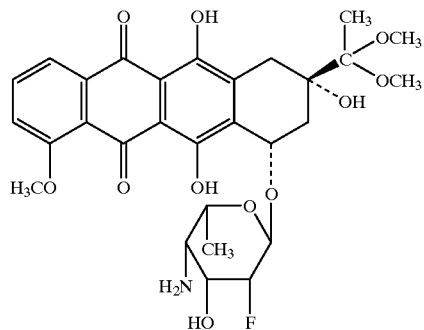

(IV)

wherein Y' is acetyl or benzoyl group as a hydroxyl-protecting group, Y" is trifluoroacetyl group as an amino-protecting group and X is bromine or iodine atom, in an organic solvent in the presence of a condensation catalyst to produce a 7-O-(3,4-di-O,N-protected-4-amino-2,4,6-trideoxy-2-fluoro-α-L-talopyranosyl)daunomycinone represented by the following formula and reacting the compound of the formula (IV) with bromine to form a compound having the following formula

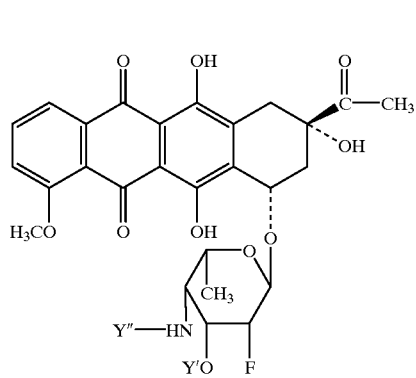

(Ia')

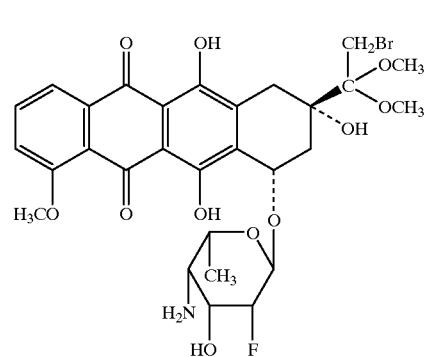

(V)

wherein Y' and Y" have the same meanings as defined above, and then removing the remaining hydroxyl-protecting group (Y') and amino-protecting group (Y") from the resulting condensation product of the formula (Ia').

followed by either hydrolyzing the compound of the formula (V) with hydrobromic acid or subjecting the compound of the formula (V) to a transketalation with acetone, thereby to remove the dimethylketal group therefrom and produce a compound of the following formula Further, the preparation of 7-O-(4-amino-2,4,6-trideoxy-2-fluoro-α-L-talopyranosyl)adriamycinone of formula (Ib) according to the first aspect of this invention, i.e. Compound (b) of this invention, may be effected by an application of a known process for converting the 14-methyl group of the daunomycinone derivative of the formula (Ia) into a hydroxymethyl group (refer to Japanese Patent Application first publication Kokai Hei 1-299296 or U.S. Pat. No. 4,125,607).

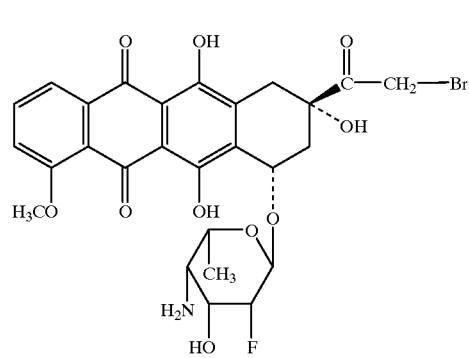

(VI)

According to a fourth aspect of this invention, therefore, there is provided, as a process for the preparation of the adriamycinone derivative of formula (Ib) according to the first aspect of this invention, i.e. Compound (b) of this invention, a process for the preparation of 7-O-(4-amino-2, 4,6-trideoxy-2-fluoro-α-L-talo-pyranosyl)adriamycinone of the formula (Ib), which comprises the steps of reacting 7-O-(4-amino-2,4,6-trideoxy-2-fluoro-α-L-talopyranosyl) daunomycinone of the formula (Ia) with methyl orthoformate for dimethylketalation of the 13-carbonyl group of the compound of the formula (Ia), thereby to produce a compound having the following formula and then hydrolyzing the resulting compound of the formula (VI) to convert the group —$CH_2$—Br thereof into a group —$CH_2OH$.

In the above process according to the fourth aspect of this invention for the preparation of the compound of formula (Ib) of this invention, the step for dimethyl-ketalation of the 13-carbonyl group of the daunomycinone derivative of formula (Ia), which is used as starting material, may be carried out by reacting the daunomycinone derivative of formula (Ia) with methyl orthoformate in methanol, dioxane or their mixture at a temperature of 0° C.~50° C. Subsequently, the resulting compound of formula (IV) is reacted with bromine in a halogenated hydrocarbon such as dichloromethane, a lower alkanol such as methanol, or dioxane or tetrahydrofuran at a temperature of 0° C.~50° C. to form the compound of formula (V). For the removal of the dimethylketal group, the compound of formula (V) is then treated with hydrobromic acid or acetone, thereby to give the compound of formula (VI).

The compound of formula (VI) is further reacted with sodium formate or lithium formate to hydrolyze the 14-bromomethyl group (—CH$_2$—Br) into a hydroxymethyl group. The reaction with sodium formate or lithium formate is carried out at 0° C.~50° C. for 1~48 hours in water or a solvent comprising dimethylsulfoxide, dimethylformamide, ethers such as dioxane, tetrahydrofuran, etc. and ketones such as acetone, and the like. If a formyloxy group was occasionally introduced at the 14-position of the so formed adriamycinone derivative as a side reaction occurred, then the decomposition of the formyloxy group may be achieved by subjecting the reaction mixture to a hydrolytic treatment with aqueous ammonia or aqueous sodium hydrogen carbonate (according to a modification of Arcamone's method shown in Example 1 of Japanese Patent Application first publication Kokai Hei 1-299296 or U.S. Pat. No. 4,125,607). Thus, there is afforded the adriamycinone derivative of formula (Ib) according to the first aspect of this invention (refer to Example 3 hereinafter given).

Further, according to a fifth aspect of this invention, there is provided a use of the daunomycinone or adriamycinone derivative represented by the general formula (I) defined hereinbefore or a pharmaceutically acceptable acid addition salt thereof, in the manufacture of a pharmaceutical composition, particularly an antitumor composition.

Further, the sugar halides of general formula (III) shown hereinbefore are new compounds and are useful as intermediates utilizable for the synthesis of the anthracycline derivatives of the general formula (I). Therefore, in a sixth aspect of this invention, there is provided a 3,4-di-O,N-protected -4-amino-2,4,6-trideoxy-2-fluoro-L-talopyranosyl halide represented by the following general formula

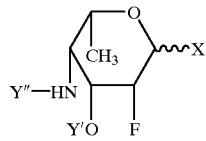

(III)

wherein Y' is acetyl or benzoyl group, Y" is trifluoroacetyl group and X is bromine or iodine atom.

This invention will now be illustrated more concretely with reference to Example 1 which describes an example of the synthesis of the various 4-amino-2,4,6-trideoxy-2-fluoro-α-L-talopyranose derivatives, as well as to Examples 2 and 3 which describe examples of the synthesis of the novel anthracycline derivatives of formulae (Ia) and (Ib) according to this invention. In the formulae shown in these Examples 1~3, Bn stands for benzyl proup and Ac stands for acetyl group.

EXAMPLE 1

(1) Preparation of benzyl 3,4-di-O-acetyl-2,6-dideoxy-2-fluoro-β-L-talopyranoside [Compound (2)] and -α-L-talopyranoside [Compound (3)]

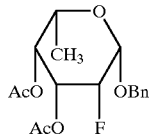

Compound (2)

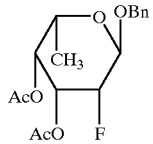

Compound (3)

3,4-Di-O-acetyl-2,6-dideoxy-2-fluoro-α-L-talopyranosyl bromide [Compound (1)] (a compound described by K. Ok, Y. Takagi, T. Tsuchiya, S. Umezawa and H. Umezawa in the "Carbohydrate Research" Vol. 169, pp. 69–81(1987)) (2.50 g) was dissolved in 53 ml of anhydrous benzene. The resulting solution was added with benzyl alcohol (5.3 ml), silver carbonate (7.24 g), iodine (5.27 g) and powdery Molecular Sieves (6.16 g) and then stirred at 50° C. in dark place for 16 hours to effect the reaction intended.

The resulting reaction solution was diluted with benzene and then filtered through Celite, and the Celite was washed with benzene. The filtrate and the benzene washings were combined together, and the resulting solution in benzene was washed successively with an aqueous 20% solution of sodium thiosulfate, a saturated aqueous solution of sodium hydrogen carbonate and water and then dried over anhydrous sodium sulfate. The dried solution was further distilled under a reduced pressure to remove the solvent therefrom. The residue obtained was recrystallized from ethyl acetate-hexane to afford 1.56 g of the titled Compound (2) as needles.

The mother liquor obtained upon the recrystallization was concentrated under a reduced pressure, and the residue was subjected to a silica gel column chromatography (development solvent: toluene-ethyl acetate, 12:1) for the separation and purification of the desired products. Thereby, 0.12 g of a second crop of Compound (2) (totally 1.68 g, total yield 62%) was obtained and 0.68 g (yield 25%) of the titled Compound (3) was obtained as a syrup.

Compound (2)

Melting point: 122.5–124.5° C.

$[\alpha]_D^{25}$ +95° (c 0.1, chloroform)

$^1$H-NMR spectrum (in deutero-chloroform): δ2.1, 2.2 (each 3H, s, Ac) 4.46 (1H, d, $J_{1,F}$=18.5 Hz, H-1) 4.72, 5.0 (each 1H, d, CH$_2$ of benzyl group)

$^{19}$F-NMR spectrum (in deutero-chloroform, CFCl$_3$ as internal standard: δ–219.3 (ddd)

Elemental analysis (for C$_{17}$H$_{21}$FO$_6$): Calculated: C, 59.99; H, 6.22; F, 5.58% Found: C, 60.18; H, 6.10; F, 5.60%

Compound (3)

$[\alpha]_D^{24}$ –85° (c 1.2, chloroform)

$^1$H-NMR spectrum (in deutero-chloroform): δ2.07, 2.16 (each 3H, s, Ac) 5.12 (1H, dd, $J_{1,F}$=9.5, $J_{1,2}$=2 Hz) 4.57, 4.71 (each 1H, d, CH$_2$ of benzyl group)

$^{19}$F-NMR spectrum (in deutero-chloroform, CFCl$_3$ as internal standard: δ–202.6 (ddd)

Elemental analysis (for C$_{17}$H$_{21}$FO$_6$): Calculated: C, 59.99; H, 6.22; F, 5.58% Found: C, 60.06; H, 6.14; F, 5.41%

(2) Preparation of benzyl 2,6-dideoxy-2-fluoro-β-L-talopyranoside [Compound (4)]

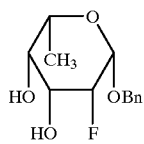

Benzyl 3,4-di-O-acetyl-2,6-dideoxy-2-fluoro-β-L-talopyranoside (1.66 g) obtained in Example 1-(1) above was suspended in 50 ml of anhydrous methanol. The resulting suspension was added with 0.5 ml of a solution of 4.9 M sodium methoxide in methanol and then stirred at room temperature for 30 minutes to effect the reaction intended. The homogenous reaction solution so obtained was neutralized by addition thereto of an ion-exchange resin, Dowex 50 W×2 (H$^+$-form) and then filtered to remove the resin therefrom. The filtrate obtained was concentrated to a small volume and the concentrated solution was allowed to stand at −10° C. and the deposited needles were separated by filtration, affording 1.11 g (yield 89%) of the titled Compound (4).

Melting point: 124–126° C.
$[\alpha]_D^{25}$ +104° (c 1, chloroform)
Elemental analysis (for $C_{13}H17FO_4$): Calculated: C, 60.93; H, 6.69; F, 7.41% Found: C, 60.84; H, 6.89; F, 7.63%

(3) Preparation of benzyl 3-O-benzyl-2,6-dideoxy-2-fluoro-β-L-talopyranoside [Compound (5)]

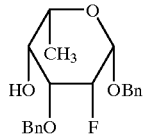

Benzyl 2,6-dideoxy-2-fluoro-β-L-talopyranoside (1.08 g) obtained in Example 1-(2) above and dibutyltin oxide (1.41 g) were dissolved in 110 ml of anhydrous benzene. The resulting solution was placed in a reaction vessel, and a dropping funnel provided with a side tube containing Molecular Sieves 4A therein was inserted into between said reaction vessel and a cooling condensor. The solution in the reaction vessel was refluxed for 5 hours while water as formed was eliminated outwards.

The reaction solution so obtained was concentrated to about a half volume under a reduced pressure, and the resulting concentrated solution was then added with benzyl bromide (1.5 ml) and tetrabutylammonium iodide (901 ml) and again refluxed for 5 hours using the above-mentioned apparatus. The resulting reaction solution was concentrated under a reduced pressure and the residue obtained was dissolved in chloroform. The solution in chloroform was then washed successively with an aqueous 20% solution of sodium thiosulfate and an aqueous 20% solution of sodium chloride and dried over anhydrous sodium sulfate. The dried solution was concentrated under a reduced pressure. The residue obtained was subjected to a silica gel column chromatography (development solvent: chloroform-ethyl acetate, 15:1) for the purification. The desired fractions of the eluate from the silica gel column were combined and concentrated to dryness under a reduced pressure, and the residue was recrystallized from diethyl ether-hexane to afford 1.33 g (yield 91%) of the titled Compound (5) as needles.

Melting point: 73.5–74.5° C.
$[\alpha]_D^{20}$ +65° (c 1, chloroform)

$^1$H-NMR spectrum (in deutero-chloroform): δ2.83 (1H, t, $J_{4,OH-4}=J_{F,OH-4}=8.5$ Hz, OH-4) 4.66, 4.68, 4.76, 4.96: (each 1H, d, CH$_2$ of benzyl group)

$^{19}$F-NMR spectrum (in deutero-chloroform, CFCl$_3$ as internal standard): δ−217.5 (dddd)

Elemental analysis (for $C_{20}H_{23}FO_4$): Calculated: C, 69.35; H, 6.69; F, 5.48% Found: C, 69.03; H, 6.91; F, 5.50%

(4) Preparation of benzyl 3-O-benzyl-2,6-dideoxy-β-L-lyxo-hexopyranose-4-uloside [Compound (6)]

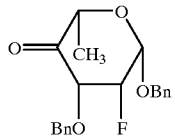

Benzyl 3-O-benzyl-2,6-dideoxy-2-fluoro-β-L-talopyranoside (98 mg) as obtained in Example 1-(3) above was dissolved in 2 ml of anhydrous dichloromethane. The resulting solution was added with pyridinium chlorochromate (164 mg) and powdery Molecular Sieves 4A (331 mg), and the mixture obtained was stirred at room temperature for 2 hours to effect the reaction intended.

The resulting reaction solution of a blackish brown color was diluted with ethyl ether, and the diluted solution was filtered twice through layers of Kiesel gel 60G (Art 7731, a silica gel product of Merck Co., U.S.A.). The resulting filtrate was concentrated under a reduced pressure, and the residue obtained was recrystallized from diethyl ether-hexane to give 66 mg (yield 68%) of the titled Compound (6).

Melting point: 96.5–97.5° C.
$[\alpha]_D^{23}$ +27° (c 1, chloroform)
IR spectrum (KBr): 1740 cm$^{-1}$ (C═O)
$^{19}$F-NMR spectrum (in deutero-chloroform, CFCl$_3$ as Internal standard): δ−212.5 (ddd)
Elemental analysis (for $C_{20}H_{21}FO_4$): Calculated: C, 69.74; H, 6.16; F, 5.52% Found: C, 69.69; H, 6.13; F, 5.31%

(5) Preparation of benzyl 3-O-benzyl-2,4,6-trideoxy-2-fluoro-4-(methoxyimino)-β-L-lyxo-hexopyranoside [Compound (7)]

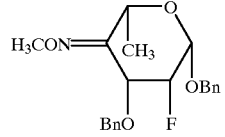

Benzyl 3-O-benzyl-2,6-dideoxy-β-L-lyxo-hexopyranose-4-uloside (654 mg) was dissolved in 6.5 ml of anhydrous pyridine. The resulting solution was added with O-methylhydroxyammonium chloride (243 mg) and then stirred at room temperature for 2.5 hours to effect the reaction intended.

The reaction solution was concentrated under a reduced pressure and the concentrated solution was then added with chloroform. The resulting solution in chloroform was washed with water, dried over anhydrous sodium sulfate and concentrated under a reduced pressure. The residue obtained was purified by a silica gel column chromatography (development solvent: toluene) to afford 612 mg (yield 86%) of the titled Compound (7) as a syrup.

$[\alpha]_D^{23}$ +61° (c 1, chloroform)
$^1$H-NMR spectrum (in deutero-chloroform): δ3.93, (3H, s, OCH$_3$)

(6) Preparation of benzyl 3-O-benzyl-2,4,6-trideoxy-2-fluoro-4-(trifluoroacetamido)-β-L-talopyranoside [Compound (9)]

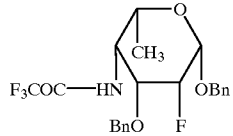

A suspension of lithium borohydride (183 mg) in anhydrous tetrahydrofuran (10 ml) was added with chlorotrimethylsilane (2.7 ml) under an atmosphere of nitrogen gas at −20° C. and then stirred at room temperature for 2 hours. The resultant suspension was again cooled to −20° C. and then added with a solution of Compound (7) obtained in Example 1-(5), namely benzyl 3-O-benzyl-2,4,6-trideoxy-2-fluoro-4-(methoxyimino)-β-L-lyxo-hexopyranoside (612 mg) in anhydrous tetrahydrofuran (10 ml). The resulting mixture was stirred at room temperature for 17 hours.

The reaction solution so obtained was added with methanol (4.5 ml) and triethylamine (3.5 m) and then stirred for 30 minutes and thereafter concentrated under a reduced pressure. Thus, there was obtained a solid comprising benzyl 4-amino-3-O-benzyl-2,4,6-trideoxy-2-fluoro-β-L-talopyranoside [Compound (8)]. This solid gave a ninhydrin-positive spot at Rf 0.45 on a silica gel thin layer chromatography as developed with chloroform-methanol-9% aqueous ammonia (20:1:1) as the development solvent.

Subsequently, this solid was suspended in mixture of anhydrous dichloromethane (24 ml) and anhydrous pyridine (5.5 ml), and the resulting suspension was added with trifluoroacetic anhydride (2.5 ml) at 0° C. and stirred at room temperature for 15 hours. Then, the. reaction had not yet been completed. And hence, said suspension was added further with anhydrous pyridine (2.0 ml) and trifluoroacetic anhydride (1.0 ml) and then stirred for 3 hours.

The reaction solution so obtained was added with methanol (3.1 ml) and stirred at room temperature for 30 minutes. Thereafter, the solution was diluted with chloroform and washed successively with a saturated aqueous solution of sodium hydrogen carbonate, an aqueous 20% solution of potassium hydrogen sulfate and water, followed by drying over anhydrous sodium sulfate and concentrating under a reduced pressure. The residue obtained was purified by a silica gel column chromatography (development solvent: toluene-acetone, 50:1) to afford 450 mg (a yield of 62% from Compound 7) of the titled Compound (9) as a syrup.

$[\alpha]_D^{23}$ +18° (c 0.7 chloroform)

$^1$H-NMR spectrum (in deutero-chloroform): δ3.50 (1H, ddd, $J_{2,3}$=2, $J_{3,4}$=4.5, $J_3,F$=32 Hz, H-3) 3.59 (1H, dq, $J_{4,5}$=2, $J_{5,6}$=6.5 Hz, H-5)

$^{19}$F-NMR spectrum (in deutero-chloroform CFCl$_3$ as internal standard): δ−217.7 (1F, dddd, F-2) −76.3 (3F, s, CF$_3$)

Elemental analysis (for $C_{22}H_{23}FNO_4$): Calculated: C, 59.85; H, 5.26; F, 17.22; N, 3.17% Found: C, 59.54; H, 5.30; F, 17.29; N, 3.35%

(7) Preparation of 2,4,6-trideoxy-2-fluoro-4-(trifluoroacetamido)-L-talopyranose [Compound (10)]

Elemental analysis (for $C_{21}H_{24}FNO_6$): Calculated: C, 67.53; H, 6.49; F, 5.09; N, 3.75% Found: C, 67.35; H, 6.49; F, 5.21; N, 4.07%

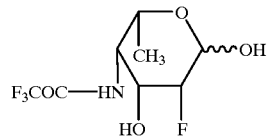

Benzyl 3-O-benzyl-2,4,6-trideoxy-2-fluoro-4-(trifluoroacetamido)-β-L-talopyranoside (581 mg) obtained in Example 1-(6) above was dissolved in 18 ml of a mixture of 1,4-dioxane-acetic acid-water (10:1:1). The resulting solution was added with palladium black and then was subjected to hydrogenolysis reaction at room temperature under agitation with hydrogen gas being blown into the solution for 9 hours.

The resulting reaction solution was filtered for removal of the catalyst and then concentrated under a reduced pressure. The residue obtained was added with toluene and concentrated under a reduced pressure, followed by repeating the addition of toluene and concentration under reduced pressure several times. In this way, a syrup of the titled Compound (10) as a mixture of the two anomers was obtained in a quantative yield of 344 mg.

$[\alpha]_D^{24}$ −62° (c 0.6, methanol, 24 hours later from dissolution)

$^{19}$F-NMR spectrum (in deutero-chloroform, CFCl$_3$ as internal standard δ−218.9 (0.25F, dddd, $J_{1,F}$=22.5, $J_{2,F}$=51.5, $J_{3,F}$=34.5, $J_{NH,F}$=8 Hz, β-L-anomer's F-2) −198.9 (0.75F, apparently ddt, $J_{1,F}$=10, $J_{2,F}$=51.5, $J_{3,F}$=36.5, $J_{NH,F}$=~7.5 Hz, α-L-anomer's F-2) −74.61 (0.75F, s, β-L-anomer's CF$_3$) −74.55 (2.25F, s, α-L-anomer's CF$_3$)

Elemental analysis (for $C_8H_{11}F_4NO_4$): Calculated: C, 36.78; H, 4.25; F, 29.10; N, 5.36% Found: C, 36.80; H, 4.50; F, 29.19; N, 5.18%

(8) Preparation of 1,3-di-O-acetyl-2,4,6-trideoxy-2-fluoro-4-(trifluoroacetamido)-α-L-talopyranose [Compound (11)] and -β-L-talopyranose [Compound (12)]

Compound (11)

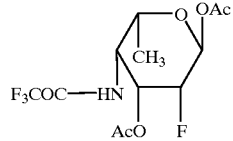

Compound (12)

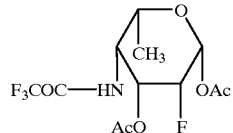

2,4,6-Trideoxy-2-fluoro-4-(trifluoroacetamido)-L-talopyranose (310 mg) obtained in Example 1-(7) and acetic anhydride (0.68 ml) were dissolved in 3.2 ml of anhydrous pyridine. The resulting solution was allowed to stand at room temperature for 3 hours.

The reaction solution so obtained was added with water (0.7 ml) and then allowed to stand for 30 minutes, followed by concentrating under a reduced pressure. The residue obtained was diluted with chloroform. The resulting solution in chloroform was washed successively with an aqueous 20% solution of potassium hydrogen sulfate, a saturated aqueous solution of sodium hydrogen carbonate and water and then dried over anhydrous sodium sulfate and concentrated under a reduced pressure. The residue obtained was subjected to a silica gel column chromatography (development solvent: chloroform-acetone, 30:1) for the separation and purification of the desired products. Thereby, there were obtained 337 mg (yield 82%) of the titled Compound (11) and 69 mg (yield 17%) of the titled Compound (12), respectively, as a syrup.

Compound (11)

$[\alpha]_D^{26}$ −69° (c 1, chloroform)

¹H-NMR spectrum (in deutero-chloroform): δ2.12, 2.16 (each 3H, s, Ac) 6.30 (1H, dd, $J_{1,2}$=2, $J_{1,F}$=8.5 Hz, H-1)

Elemental analysis (for $C_{12}H_{15}F_4NO_6$): Calculated: C, 41.74; H, 4.39; F, 22.01; N, 4.06% Found: C, 41.46; H, 4.35; F, 21.81; N, 4.12%

Compound (12)

$[\alpha]_D^{24}$ +1.8° (c 0.9, chloroform)

¹H-NMR spectrum (in deutero-chloroform): δ2.12, 2.21 (each 3H, s, Ac) 5.74 (1H, br d, $J_{1,F}$=21 Hz, H-1)

Elemental analysis (for $C_{12}H_{15}F_4NO_6$): Calculated: C, 41.74; H, 4.39; F, 22.01; N, 4.06% Found: C, 41.41; H, 4.41; F, 22.32; N, 4.12%

(9) Preparation of 3-O-acetyl-2,4,6-trideoxy-2-fluoro-4-(trifluoroacetamido)-α-L-talopyranosyl bromide [Compound (13)]

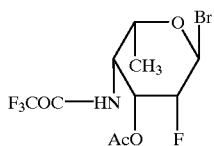

1,3-Di-O-acetyl-2,4,6-trideoxy-2-fluoro-4-(trifluoroacetamido)-L-talopyranose [the mixture of Compounds (11) and (12)] (335 mg) obtained in Example 1-(8) above was dissolved in 3.4 ml of a solution of 30% hydrogen bromide in acetic acid. The resultant solution was allowed to stand at room temperature for 1 hour to effect the bromination reaction.

The resulting reaction solution was diluted with dichloromethane and then washed successively with cold water, a cold saturated aqueous solution of sodium hydrogen carbonate and cold water. The washed solution was dried over anhydrous sodium sulfate and concentrated under a reduced pressure. In this way, the titled compound (13) was obtained as a solid in a yield of 335 mg (94%).

¹H-NMR spectrum (in deutero-chloroform): δ2.11 (3H, s, Ac) 6.47 (1H, dd, $J_{1,2}$=1, $J_{1,F}$=12 Hz, H-1)

¹⁹F-NMR spectrum (in deutero-chloroform, CFCl₃ as internal standard): δ−178.8 (1F, dddd, F-2) −76.4 (3F, s, CF₃)

EXAMPLE 2

(1) Preparation of 7-O-[3-O-acetyl-2,4,6-trideoxy-2-fluoro-4-(trifluoroacetamido)-α-L-talopyranosyl]daunomycinone [Compound (14)]

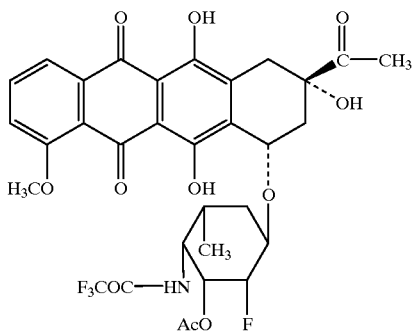

3-O-Acetyl-2,4,6-trideoxy-2-fluoro-4-(trifluoroacetamido)-α-L-talopyranosyl bromide (319 mg) as obtained in Example 1-(9) above, daunomycinone (495 g), yellow mercuric oxide (854 mg), mercuric bromide (237 mg) and powdery Molecular Sieves 3A (3.67 g) were suspended in 100 ml of anhydrous dichloromethane. The resulting suspension was refluxed in a dark place for 17 hours and then added further with yellow mercuric oxide (927 mg) and mercuric bromide (306 mg) and thereafter was concentrated until the volume of the solvent present was reduced to about ⅔-th of the orignal volume. Subsequently, the concentrated suspension was refluxed in a dark place for 79 hours.

The resulting reaction solution was filtered through Celite, and the Celite was washed with chloroform. The resulting filtrate and the washings in chloroform were combined, and the solution so obtained was washed successively with an aqueous 30% solution of potassium iodide, a saturated aqueous solution of sodium hydrogen carbonate and water. The washed solution was dried over anhydrous sodium sulfate and concentrated under a reduced pressure. The residue obtained was subjected to a silica gel column chromatography (development solvent: chloroform-acetone, 15:1) for the separation and purification of the target compound. When the solid product obtained was re-precipitated from chloroform-hexane, the titled Compound (14) was afforded as a red solid in a yield of 260 mg (44%).

$[\alpha]_D^{23}$ +190° (c 0.03, chloroform)

¹H-NMR spectrum (in deutero-chloroform): δ2.04 (3H, S, OAc) 2.42 (3H, s, Ac) 4.09 (3H, s, OMe) 4.69 (1H, br d, H-2') 5.60 (1H, dd, $J_{1',2'}$=1.5, $J_{1',F}$=10 Hz, H-1')

¹⁹F-NMR spectrum (in deutero-chloroform, CFCl₃ as internal standard:

δ−198.7 (1F, dddd, F-2') −76.4 (3F, s, CF₃)

Elemental analysis (for $C_{31}H_{29}F_4NO_{12}·0.1 H_2O$): Calculated: C, 54.32; H. 4.30; F, 11.09; N, 2.04% Found: C, 54.03; H, 4.09; F, 10.92; N, 2.08%

(2) Production of 7-O-(4-amino-2,4,6-trideoxy-2-fluoro-α-L-talopyranosyl)daunomycinone [Compound (15), namely Compound (a) of this invention]

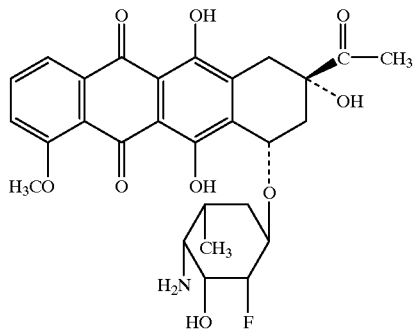
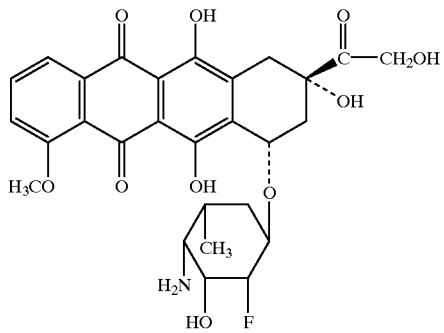

Compound (14) obtained in Example 2-(1) above, namely 7-O-[3-O-acetyl-2,4,6-trideoxy-2-fluoro-4-(trifluoroacetamido)-α-L-talopyranosyl]daunomycinone (240 mg) was suspended in 24 ml of an aqueous solution of 0.23N sodium hydroxide. The resulting suspension was stirred at 0° C. for 3 hours under argon atmosphere to effect the reaction (for the reaction of removing the protective groups).

The resultant reaction solution was added with 5.7 ml of 1N hydrochloric acid and then washed with chloroform. The aqueous solution so washed was added with a saturated aqueous solution of sodium hydrogen carbonate to adjust pH of the solution to about 8. Said aqueous solution was thereafter extracted with chloroform, and the resulting chloroform solution (the extract) was washed with water and dried over anhydrous sodium sulfate. The dried solution was then concentrated under a reduced pressure.

The residue so obtained was dissolved in a mixture of chloroform-methanol (2:1), to which was then added 0.7 ml of a solution of 2.3N hydrogen chloride in methanol. The resulting mixture was added with isopropyl ether to effect re-precipitation of the desired compound, affording 175 mg (yield 88%) of the titled Compound (15) as its hydrochloride in the form of a red solid.

$[\alpha]_D^{24}$ +240° (c 0.01, methanol)

$^1$H-NMR spectrum (in deutero-methanol): δ2.37 (3H, s, Ac) 3.98 (3H, s, OMe) 4.64 (1H, br d, H-2') 5.51 (1H, br d, H-1')

$^{19}$F-NMR spectrum (in deutero-methanol, $CFCl_3$ as internal standard): δ−201.3 (ddd)

Elemental analysis (for $C_{27}H_{28}NFO_{10} \cdot HCl \cdot 1.3H_2O$): Calculated: C, 53.56; H, 5.27; Cl, 5.86; F, 3.14; N, 2.31% Found: C, 53.61; H, 5.49; Cl, 5.85; F, 3.14; N, 2.01%

EXAMPLE 3

Production of 7-O-(4-amino-2,4,6-trideoxy-2-fluoro-α-L-talopyranosyl)adriamycinone [Compound (16), namely Compound (b) of this invention]

Compound (a) of this invention as obtained in Example 2, namely 7-O-(4-amino-2,4,6-trideoxy-2-fluoro-α-L-talopyranosyl)daunomycinone [Compound (15)], (47.6 mg) was dissolved in a mixture of anhydrous methanol (1 ml) and anhydrous 1,4-dioxane (1.7 ml). The resulting solution was added with methyl orthoformate (54 μl) and the mixture was stirred at room temperature for 20 minutes (for the protection of the 13-carbonyl group by the ketalation).

Then, the resulting reaction solution was cooled to 0° C. and was added with a solution of bromine (22 mg) in anhydrous dichloromethane (0.2 ml). The mixture obtained was stirred at room temperature for 2 hours, thereby to conduct the bromination at the 14-position of the compound.

To the resultant reaction solution were added isopropyl ether (15 ml) and hexane (5 ml) to deposit a red precipitate, which was then separated centrifugally and washed twice with hexane. The precipitate was then suspended in acetone (5 ml) and the suspension was stirred at room temperature for 2 hours for conducting the deketalation reaction. To the resulting reaction solution was added hexane to deposit a precipitate, which was then recovered by centrifugation.

The precipitate obtained was taken up into a mixture of water (1.5 ml) and acetone (1 ml), and the resultant solution was added with sodium formate (101 mg) and then stirred at room temperature for 22 hours to effect the reaction intended. The reaction solution was concentrated under a reduced pressure to distill acetone from the solution. The remaining aqueous solution was washed with chloroform. The chloroform solution obtained (as the washing) was further washed twice with water. The aqueous washings so obtained were combined with said aqueous solution, and the resultant mixture was charged into a column packed with 20 ml of a non-ionic adsorbent resin, Diaion HP20 (a product of Mitsubishi Kasei Co., Japan). The resin column was then washed with water for the de-salting and was subsequently eluted with development solvents comprising water, aqueous methanol or methanol, while the concentration of methanol in the development solvents was changed from 0% to 100% gradually. The active fractions of the eluate containing the target compound were thus recovered and combined, followed by concentrating under a reduced pressure.

The residue obtained was dissolved in a mixture of chloroform-methanol (2:1), to which was then added a solution of 2N hydrogen chloride in methanol to adjust to pH 1. The solution having the adjusted pH of 1 was then added with isopropyl ether to allow a precipitate to deposit. The precipitate was recovered by centrifugation to afford 28.2 mg (yield 58%) of the titled Compound (16) as its hydrochloride in the form of a red solid.

$[\alpha]_D^{23}$ +260° (c 0.01, methanol)

$^1$H-NMR spectrum (in deutero-methanol): δ3.73 (3H, s, OMe) 4.77 (1H, br d, H-2') 4.78, 4.83 (each 1H, d, J=20 Hz, H-14a, 14b) 5.48 (1H, br d, H-1')

$^{19}$F-NMR spectrum (in deutero-methanol, CFCl$_3$ as internal standard): δ−201.3 (ddd)

Elemental analysis (for C$_{27}$H$_{28}$NFO$_{11}$·HCl·H$_2$O): Calculated: C, 52.64; H, 5.08; Cl, 5.75; F, 3.09; N, 2.27% Found: C, 52.54; H, 5.20; Cl, 5.99; F, 2.99; N, 2.32%.

What is claimed is:

1. A 3,4-di-O,N-protected-4-amino-2,4,6-trideoxy-2-fluoro-L-talopyranosyl halide represented by the following formula

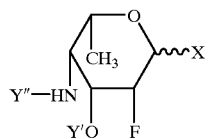

(III)

wherein Y' is acetyl or benzoyl group, Y" is trifluoroacetyl group and X is bromine or iodine atom.

2. A process of preparing a 3,4-di-O,N-protected-4-amino-2,4,6-trideoxy-2-fluoro-L-talopyranosyl halide of the formula

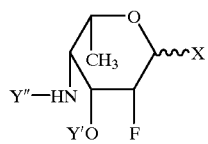

(III)

wherein Y' is acetyl or benzoyl group, Y" is trifluoroacetyl group and X is bromine or iodine atom, which comprises consecutive steps of oxidizing benzyl 3-O-benzyl-2,6-dideoxy-2-fluoro-β-L-talopyranoside (Compound (5)) of the formula

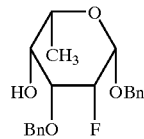

wherein Bn denotes benzyl group, with pyridinium chlorochromate to produce benzyl 3-O-benzyl-2,6-dideoxy-2-fluoro-β-L-lyxo-hexopyranose-4-uloside (Compound (6)) of the formula

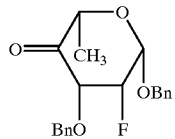

where Bn denotes benzyl group, reacting this Compound (6) with O-methylhydroxyammonium chloride in anhydrous dichloromethane to produce benzyl 3-O-benzyl-2,4,6-trideoxy-2-fluoro-4-(methoxyimino)-β-L-lyxo-hexopyranoside (Compound (7)) of the formula

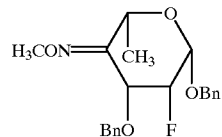

wherein Bn is as defined above, as the 4-methoxyiminoated product, reducing this Compound (7) with lithium borohydride in the presence of chlorotrimethylsilane to bring about the reduction with a steric selectivity and produce benzyl 4-amino-3-O-benzyl-2,4,6-trideoxy-2-fluoro-β-L-talopyranoside (Compound (8)) of the formula

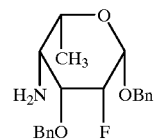

wherein Bn is as defined above, as a 4-amino-sugar having the L-talo configuration, reacting this Compound (8) with trifluoroacetic anhydride to protect the amino group of Compound (8) with trifluoroacetyl group and produce benzyl 3-O-benzyl-2,4,6-trideoxy-2-fluoro-4-(trifluoroacetamido)-β-L-talopyranoside (Compound (9)) of the formula

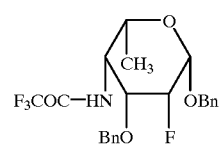

wherein Bn is as defined above, subjecting this Compound (9) to hydrogenolysis in the presence of a palladium catalyst to remove the two benzyl groups from Compound (9) and to produce 2,4,6-trideoxy-2-fluoro-4-(trifluoroacetamido)-L-talopyranose Compound (10) having the formula

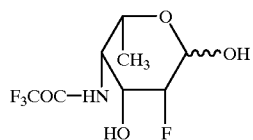

then reacting this Compound (10) with acetic anhydride or benzoyl chloride in anhydrous pyridine to produce an anomer mixture of 1,3-di-O-protected -2,4,6-trideoxy-2-fluoro-4-(trifluoroacetamido)-α-L-talopyranose (Compound (11')) having the formula

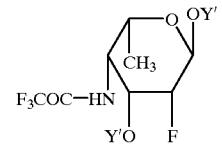

and 1,3-di-O-protected-2,4,6-trideoxy-2-fluoro-4-(trifluoroacetamido)-β-L-talopyranose (Compound (12')) having the formula

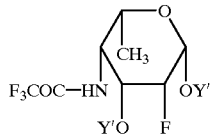

wherein Y' is acetyl group or benzoyl group, and brominating the anomer mixture of Compound (11') and Compound (12') with a solution of hydrogen bromide in acetic acid or iodinating said anomer mixture with iodotrimethylsilane in anhydrous toluene to produce a 3-O-protected-2,4,6-trideoxy-2-fluoro-4-(trifluoroacetamido)-α-L-talopyranosyl halide having the formula

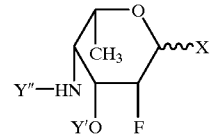

(III)

wherein Y' is acetyl or benzoyl group, Y" is trifluoroacetyl group $F_3COC-$ and X is bromine or iodine atom.

3. 2,4,6-Trideoxy-2-fluoro-4-(trifluoroacetamido)-L-talopyranose having the formula

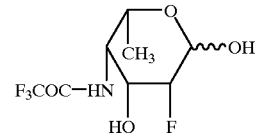

* * * * *